US00PP36041P3

(12) United States Plant Patent
Olesen

(10) Patent No.: US PP36,041 P3
(45) Date of Patent: Jul. 30, 2024

(54) MINIATURE ROSE PLANT NAMED 'POULPAH123'

(50) Latin Name: *Rosa hybrida*
Varietal Denomination: Poulpah123

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,473

(22) Filed: Sep. 8, 2023

(65) Prior Publication Data

US 2024/0107912 P1 Mar. 28, 2024

(30) Foreign Application Priority Data

Sep. 30, 2022 (QZ) ..... PBR 2022/2169

(51) Int. Cl.
*A01H 5/02* (2018.01)
*A01H 6/74* (2018.01)

(52) U.S. Cl.
USPC ..... Plt./118
CPC ..... *A01H 6/749* (2018.05)

(58) Field of Classification Search
USPC ..... Plt./101, 116, 118, 123, 125
See application file for complete search history.

(56) References Cited

PUBLICATIONS https://www.poulsenroser.dk/en/Roses/ShowProduct/80001 (Katrina) (1 page).*
https://www.poulsenroser.dk/fr/Roses/ShowProduct/80001 (Katrina Hit) (1 page).*
https://pharmarosahigh-hu.translate.goog/rozsa/katrina-hit-1274? (3 pages).*

* cited by examiner

*Primary Examiner* — Susan McCormick Ewoldt

(57) ABSTRACT

A new garden rose plant of the Miniature class which has abundant, yellow-orange white flowers and attractive foliage. This new and distinct variety has shown to be uniform and stable in the resulting generations from asexual propagation.

2 Drawing Sheets

Botanical designation: *Rosa hybrida.*

Variety denomination: 'Poulpah123'.

This application claims priority to Plant Breeder's Rights Application Number 2022/2169, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah123', originated as a single seedling from the stated cross.

The new variety may be distinguished from its male pollen parent and female seed parent primarily by the following characteristics. The male pollen parent plant has apricot flowers while the new variety has yellow-orange white flowers. The female seed parent plant has yellow flowers while the new variety has yellow-orange white flowers.

The objective of the hybridization of this rose variety was to create a new and distinct variety with unique qualities, such as:

1. Uniform and abundant yellow-orange white flowers;
2. Vigorous, but compact growth when propagated on its own roots;
3. Exceptional disease resistance.

This combination of qualities is not present in previously available commercial cultivars of this type, known to the inventor, and distinguish 'Poulpah123' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah123' was selected in the spring of 2016 by the inventor as a single plant from the progeny of the aforementioned hybridization.

Asexual reproduction of 'Poulpah123' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpah123' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah123'.

Specifically illustrated in FIG. 1 of the drawings are open flowers viewed from above and the side, petals detached, sepals detached revealing reproductive flower parts, and flower buds at various stages of opening.

Figure 1:
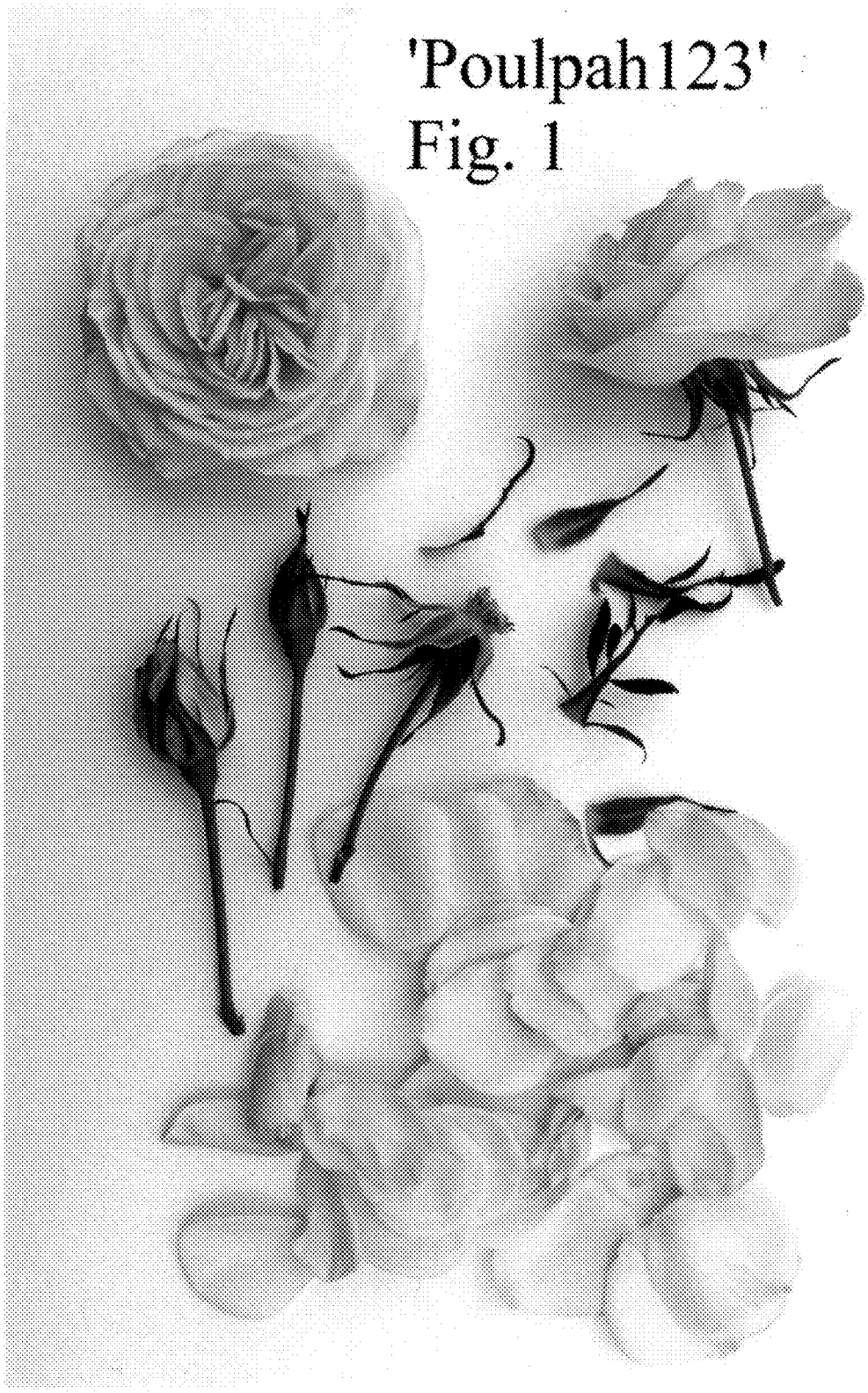
Figure 2:
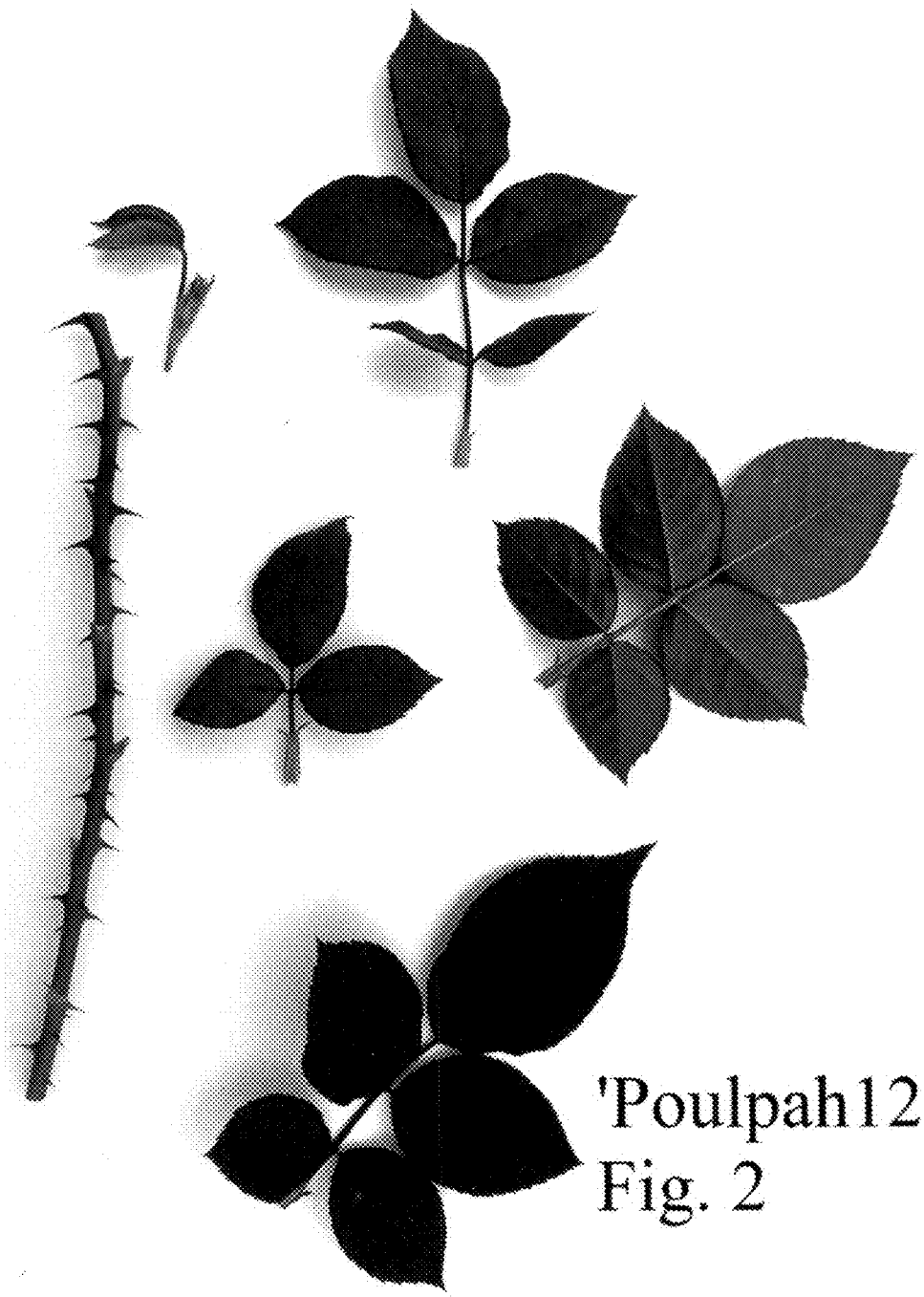

Specifically illustrated in FIG. 2 of the drawings are juvenile and mature leaves and a bare stem exhibiting prickles. Plants shown are 5 months of age.

DETAILED DESCRIPTION OF THE VARIETY

The following is a description of 'Poulpah123', as observed in its growth in an indoor glasshouse nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpah059', U.S. Plant Pat. No. 24,850 are compared to the claimed plant. While 'Poulpah123' has 112 flower petals, 'Poulpah059' has 50 flower petals. The claimed plant has a flower diameter of 100 mm while 'Poulpah059' has a flower diameter of 70 to 80 mm. Open flowers of 'Poulpah123' are generally Yellow Group 8D, Yellow Group 13C, and Orange Group 28D in color while 'Poulpah059' has a general tonality Orange Group 25 A, becoming Yellow Group 11C as flowers mature.

FLOWER AND FLOWER BUD

Blooming habit: Continuous.

Flower bud:

- *Size.*—Upon opening, 33 mm in length from base of receptacle to end of bud. Bud diameter is 16 mm.
- *Bud form.*—Ovoid.
- *Bud color.*—As sepals divide petals are Yellow Group 5C, Orange-Red Group 35A, and Orange Group 24C. Occasionally Yellow-Green Group 145B.
- *Sepal inner surface.*—Color: Yellow-Green Group 147A. Surface: Strong pubescence.
- *Sepal outer surface.*—Color: Yellow-Green Group 147B. Texture: Smooth.
- *Sepal shape.*—Apex: Cirrhose. Base: Flat at union with receptacle.
- *Sepal margin.*—Margins have very strong foliaceous appendages on three of the five sepals.
- *Sepal size.*—About 75 mm long, 7 mm wide.
- *Receptacle.*—Texture: Smooth. Size: 10 mm in height, 9 mm wide. Color: Yellow-Green Group 144A. Shape: Campanulate.
- *Pedicel.*—Surface: Smooth. Length: About 60 mm. Diameter: 3 mm on average. Color: Yellow-Green Group 144A. Strength: Strong.

Flower bud development: Flower buds are borne single.

Flower bloom:

- *Fragrance.*—None, or light floral.
- *Duration.*—The blooms have a duration on the plant of approximately 21 days. Petals fall cleanly away from plant after flowers have fully matured.
- *Size.*—Flower diameter is 100 mm when open. Flower depth is 45 mm.
- *Flower shape.*—Rosette, very double flower with many slightly overlapping petals of different sizes.
- *Shape of flower, side view.*—The upper portion is flat convex. The lower portion is flat concave.

Petalage: Under normal conditions, flowers have about 112 petals.

General tonality of flower: Open flowers are Yellow Group 8D, Yellow Group 13C, and Orange Group 28D.

Petal color:

- *Open flowers, outer petals.*—Upper surface: Yellow Group 4D, Yellow Group 4C with veins Red Group 56A. Plants grown outdoor exhibit marginal intonations of Red-Purple Group 61 C. Lower surface: Yellow Group 4D, Yellow Group 4C with veins Red Group 56A. There are marginal intonations of Red Group 51B.
- *Open flowers, inner petals.*—Upper surface: Yellow Group 10A with shades of Orange Group 29B. Plants grown outdoor exhibit marginal intonations of Red-Purple Group 61 C. Lower surface: Yellow Group 10B with shades of Orange Group 25D.

Petals:

- *Petal reflex.*—None.
- *Margin.*—Entire and uniform. Light undulations.
- *Shape.*—Broad and elliptic. Apex shape: Rounded. Base shape: Acute.
- *Size.*—55 mm (l)×53 mm (w).
- *Texture.*—Smooth.
- *Thickness.*—Average.

Petaloids:

- *Size.*—16 to 25 mm (l) by 10 to 20 mm (w).
- *Quantity.*—About 12.
- *Shape.*—Elliptical with linear base and rounded apex.
- *Color.*—Yellow Group 11A with intonations of Orange Group 29B.

Reproductive flower parts:

- *Pollen.*—None observed.
- *Anthers.*—Size: 2 mm in length. Color: Greyed-Orange Group N70A. Quantity: 45 on average.
- *Filaments.*—Color: Yellow Group 2A. Length: 5 mm.
- *Pistils.*—Length: 7 mm. Quantity: 35 on average.
- *Stigmas.*—Color: Yellow-Green Group 145D.
- *Styles.*—Color: Yellow-Green Group 145D.
- *Location of stigmas.*—Level in location relative to the length of the filaments and the height of the anthers.
- *Hips.*—None Observed.

PLANT

Plant growth: Upright. Plants are about 48 cm height, and 32 cm wide.

Stems:

- *Color of juvenile growth.*—Yellow-Green Group 144B.
- *Color of mature growth.*—Yellow-Green Group 146B.
- *Length.*—Canes are about 22 cm from the base of the plant to the flowering portion.
- *Diameter.*—About 4 mm.
- *Internodes.*—On mature canes about 30 mm between nodes.
- *Surface texture.*—Young wood: Smooth. Older wood: Smooth.

Long prickles:

- *Incidence.*—20 prickles per 10 cm of stem.
- *Size.*—Average length of prickles on mature stems is 5 mm.
- *Shape.*—Upper portion is linear. Lower portion is deep concave.
- *Color.*—Juvenile prickles: Greyed-Purple Group 183A. Mature prickles: Greyed-Purple Group 183A.

Plant foliage:

*Compound leaf.*—140 mm (l)×110 (w).

*Quantity.*—2 or 3 leaves per 10 cm of stem average.

*Leaf bearing angle to the stem.*—70 to 90 degrees.

*Color of juvenile foliage*.—Upper side: Yellow-Green Group 144A Yellow-Green Group 144A with intonations of Greyed-Purple Group 183A. with intonations of Greyed-Purple Group 183A. Lower side: Yellow-Green Group 144A.

*Color of mature foliage*.—Upper side: Yellow-Green Group 147A. Lower side: Yellow-Green Group 147B.

Plant leaves and leaflets:

*Stipules*.—Size: 14 mm long, 3 mm wide. Quantity: 2 per compound leaf. Shape: Linear, slightly broad based with outward extending apices. Margins: Finely serrated. Color: Yellow-Green Group 144B.

*Petiole*.—Length: 27 mm. Diameter: 23 mm. Upper surface color: Yellow-Green Group 144A. Lower surface color: Yellow-Green Group 144A.

*Rachis*.—Length: About 35 mm. Upper surface color: Yellow-Green Group 147B with Greyed-Purple Group 183B. Lower surface color: Yellow-Green Group 144A.

*Leaflet*.—Quantity: Normally 5 leaflets. Margins: Serrated. Size: Terminal leaflets are about 70 mm long, 39 mm wide. Shape: Generally elliptical. Base: Rounded. Apex: Aristate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah123' substantially as described and illustrated herein.

* * * * *

'Poulpah123'

'Poulpah123'